(12) United States Patent
Eisen-Nevo et al.

(10) Patent No.: US 7,714,129 B2
(45) Date of Patent: May 11, 2010

(54) METHODS OF PREPARING ANHYDROUS ARIPIPRAZOLE FORM II

(75) Inventors: Hagit Eisen-Nevo, Shoam (IL); Zhanna Pavlov, Herzeliya (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 882 days.

(21) Appl. No.: 11/529,969

(22) Filed: Sep. 29, 2006

(65) Prior Publication Data

US 2007/0161794 A1 Jul. 12, 2007

Related U.S. Application Data

(63) Continuation-in-part of application No. 11/015,068, filed on Dec. 16, 2004, now Pat. No. 7,504,504.

(60) Provisional application No. 60/530,297, filed on Dec. 16, 2003, provisional application No. 60/533,831, filed on Dec. 30, 2003, provisional application No. 60/618,404, filed on Oct. 13, 2004, provisional application No. 60/618,960, filed on Oct. 14, 2004, provisional application No. 60/722,616, filed on Sep. 29, 2005, provisional application No. 60/726,456, filed on Oct. 12, 2005, provisional application No. 60/737,092, filed on Nov. 15, 2005.

(51) Int. Cl.
*C07D 401/12* (2006.01)
(52) U.S. Cl. ...................................... 544/363
(58) Field of Classification Search .................. 544/363
See application file for complete search history.

(56) References Cited

U.S. PATENT DOCUMENTS

| 4,734,416 | A  | 3/1988  | Banno et al. |
| 5,006,528 | A  | 4/1991  | Oshiro et al. |
| 6,967,209 | B2 | 11/2005 | Mendelovici et al. |
| 2004/0192915 | A1 | 9/2004 | Tsujimori et al. |
| 2005/0058935 | A1 | 3/2005 | Kishimura et al. |
| 2005/0152981 | A1 | 7/2005 | Gleeson et al. |
| 2005/0159429 | A1 | 7/2005 | Parthasaradhi et al. |
| 2005/0203299 | A1 | 9/2005 | Aronhime et al. |
| 2005/0215585 | A1 | 9/2005 | Dolitzky et al. |
| 2005/0234071 | A1 | 10/2005 | Parthasaradhi et al. |
| 2005/0272742 | A1 | 12/2005 | Worthen et al. |
| 2005/0277650 | A1 | 12/2005 | Venkataraman et al. |
| 2006/0079689 | A1 | 4/2006 | Naddaka et al. |
| 2006/0079690 | A1 | 4/2006 | Naddaka et al. |
| 2006/0142299 | A1 | 6/2006 | Ettema et al. |
| 2006/0142579 | A1 | 6/2006 | Ettema et al. |
| 2006/0223820 | A1 | 10/2006 | Brand et al. |
| 2006/0234979 | A1 | 10/2006 | Nerurkar et al. |
| 2006/0258673 | A1 | 11/2006 | Ettema et al. |
| 2006/0258869 | A1 | 11/2006 | Deshpande et al. |
| 2006/0270683 | A1 | 11/2006 | Lohray et al. |
| 2007/0148100 | A1 | 6/2007 | Jenkins |
| 2007/0213535 | A1 | 9/2007 | Brand et al. |
| 2007/0238876 | A1 | 10/2007 | Tewari et al. |
| 2007/0272777 | A1 | 11/2007 | Samburski et al. |
| 2008/0020038 | A1 | 1/2008 | Stritzke et al. |
| 2008/0132518 | A1 | 6/2008 | Wieser et al. |

FOREIGN PATENT DOCUMENTS

| CZ | 299485 | 8/2008 |
| JP | 02-191256 | 7/1990 |
| WO | WO 03/026659 | 4/2003 |
| WO | WO 03/102009 | 12/2003 |
| WO | WO 2004/083183 | 9/2004 |
| WO | WO 2004/099152 | 11/2004 |
| WO | WO 2004/106322 | 12/2004 |
| WO | WO 2005/009990 | 2/2005 |
| WO | WO 2005/058835 | 6/2005 |
| WO | WO 2006/012237 | 2/2006 |
| WO | WO 2006/030446 | 3/2006 |
| WO | WO 2006/077584 | 7/2006 |
| WO | WO 2006/079549 | 8/2006 |
| WO | WO 2006/097343 | 9/2006 |
| WO | WO 2006/097344 | 9/2006 |
| WO | WO 2007/004061 | 1/2007 |
| WO | WO 2007/007132 | 1/2007 |
| WO | WO 2007/035348 | 3/2007 |
| WO | WO 2007/092779 | 8/2007 |
| WO | WO 2007/094009 | 8/2007 |
| WO | WO 2007/118923 | 10/2007 |
| WO | WO 2007/148191 | 12/2007 |
| WO | WO 2008/001188 | 1/2008 |
| WO | WO 2008/020453 | 2/2008 |
| WO | WO 2008/051541 | 5/2008 |
| WO | WO 2008/059518 | 5/2008 |

OTHER PUBLICATIONS

Aoki, et al., "Study On Crystal Transformation Of Aripiprazol", The Fourth Japan-Korea Symposium On Separation Technology, 1996, pp. 937-940.

(Continued)

*Primary Examiner*—James O Wilson
*Assistant Examiner*—Ebenezer Sackey
(74) *Attorney, Agent, or Firm*—Kenyon & Kenyon LLP

(57) ABSTRACT

Provided is a method of preparing aripiprazole anhydrous Form II from aripiprazole.

16 Claims, 1 Drawing Sheet

OTHER PUBLICATIONS

Bernstein, "Polymorphism In Molecular Crystals", (Clarendon Press, Oxford) 2002, pp. 117-125.

Oshiro, et al., "Novel Antipsychotic Agents with Dopamine Autoreceptor Agonist Properties: Synthesis and Pharmacology of 7-[4-(4-Phenyl-1-piperaziny)butoxy]-3,4-dihydro-2(1H)-quinolinone Derivatives", J. of Med. Chem., 1998, pp. 658-667, vol. 41.

ABILIFY® aripiprazole label, PDR 2004.

Bernstein, "Polymorphism In Molecular Crystals", (Clarendon Press, Oxford) 2002, pp. 117-125.

Banno K et al, "Studies on 2 (1H)-Quinolinone Derivatives as Neuroleptic Agents. I. Synthesis and Biological Activities of (4-Phenyl-1-Piperazinyl)-Propoxy-2 (1H)-Quinolinone Derivatives", Chemical And Pharmaceutical Bulletin, vol. 36, No. 11, pp. 4377-4388 (1988).

Communication, dated Nov. 26, 2008, regarding Third Party Observations in related European Patent Application No. 04815093.2 (EP 1613598).

US 7,714,129 B2

METHODS OF PREPARING ANHYDROUS ARIPIPRAZOLE FORM II

RELATED APPLICATIONS

This application is a continuation-in-part application of U.S. application Ser. No. 11/015,068, filed on Dec. 16, 2004 now U.S. Pat. No. 7,504,504, which claims the benefit of U.S. provisional Application Ser. Nos. 60/530,297, filed on Dec. 16, 2003; 60/533,831, filed on Dec. 30, 2003; 60/618,404, filed Oct. 13, 2004; and 60/618,960, filed on Oct. 14, 2004; and this application also claims the benefit of U.S. provisional Application Ser. Nos. 60/722,616, filed on Sep. 29, 2005; 60/726,456, filed on Oct. 12, 2005; and 60/737,092, filed on Nov. 15, 2005, hereby incorporated by reference.

FIELD OF THE INVENTION

The invention encompasses methods of preparing anhydrous aripiprazole Form II.

BACKGROUND OF THE INVENTION

Schizophrenia is the most common type of psychosis caused by excessive neurotransmission activity of the dopaminergic nervous system in the central nervous system. A number of drugs which block the neurotransmission of dopaminergic receptor in the central nervous system have been developed for use in treating schizophrenia. Among the drugs developed are phenothiazine-type compounds such as chlorpromazine, butyrophenone-type compounds such as haloperidol, and benzamide-type compounds such as sulpiride. These drugs improve so-called positive symptoms in the acute period of schizophrenia such as hallucinations, delusions, and excitations. Many drugs for treating schizophrenia, however, are not effective for improving the so-called negative symptoms which are observed in the chronic period of schizophrenia such as apathy, emotional depression, and hypopsychosis. The drugs currently used produce undesirable side effects such as akathisia, dystonia, Parkinsonism dyskinesia, and late dyskinesia, by blocking the neurotransmission of dopaminergic receptor in the striate body. Drugs that improve both the negative and positive symptoms of schizophrenia but diminish the undesirable side effect of schizophrenia are particularly desirable.

Aripiprazole is a pyschotropic drug that exhibits high affinity for dopamine $D_2$ and $D_3$, serotonin $5-HT_{1A}$ and $5-HT_{2A}$ receptors; moderate affinity for dopamine $D_4$, serotonin $5-HT_{2C}$ and $5-HT_7$, $\alpha_1$-adrenergic and histamine $H_1$ receptors; and moderate affinity for the serotonin reuptake site. Aripiprazole has no appreciable affinity for cholinergic muscarinic receptors. The mechanism of action of aripiprazole, as with other drugs having efficacy in schizophrenia, is unknown. It has been proposed, however, that the efficacy of aripiprazole is mediated through a combination of partial agonist activity at $D_2$ and $5-HT_{1A}$ receptors and antagonist activity at $5-HT_{2A}$ receptors.

U.S. Pat. No. 5,006,528 and Japanese Patent Kokai No. 02-191256 disclose that anhydride crystals of aripiprazole are typically manufactured by recrystallization of anhydride aripiprazole from ethanol or by heating aripiprazole hydrate at a temperature of 80° C.

The Proceedings of the 4th Japanese-Korean Symposium on Separation Technology (Oct. 6-8, 1996) disclosed that aripiprazole anhydride crystals may exist as Type-I and Type-II crystals. According to this reference, Type-I aripiprazole crystals can be prepared by recrystallizing aripiprazole from an ethanol solution or by heating aripiprazole hydrate at 80° C. Type-II aripiprazole crystals can be prepared by heating the Type-I crystals at 130° C. to 140° C. for 15 hours. This process is not easily applied to an industrial scale preparation of anhydride aripiprazole.

PCT publication WO 03/26659 discloses the preparation of anhydrous aripiprazole Type I and crystalline Forms A, B, C, D, E, F. and G. The powder x-ray diffraction spectrum for aripiprazole Form C has characteristic peaks at 12.6°, 13.7°, 15.4°, 18.1°, 19.0°, 20.6°, 23.5°, and 26.4° 2-theta. Typically, the process for preparing the crystalline forms comprises heating crystalline anhydrous aripiprazole. The process, however, is cumbersome because it requires crystalline anhydrous aripiprazole as the starting material. The process can include drying or heating the aripiprazole which may affect the distribution of crystalline forms and/or crystalline purity, if drying causes crystalline transformation from one crystalline form to another.

The methods of the invention provide procedures that consistently and reproducibly yield Form II consistently to increase the arsenal of crystalline forms available to the skilled artisan in preparing pharmaceutical formulations.

SUMMARY OF THE INVENTION

One embodiment of the invention encompasses a method of preparing anhydrous aripiprazole Form II comprising slurrying aripiprazole in a solvent selected from the group consisting of: $C_3$-$C_8$ ketones, THF, acetonitrile, butyl-acetate, dimethyl formamide (DMF), a mixture of tetrahydrofuran (THF) and IPA, water, diethyl ether (DEE) and acetone; heating the slurry; and isolating anhydrous aripiprazole Form II from the slurry. Optionally, the method can further comprise seeding the slurry with aripiprazole Form II prior to the heating step.

Another embodiment of the invention encompasses a method of preparing anhydrous aripiprazole Form II comprising providing a mixture of aripiprazole in acetone; heating the mixture at a temperature of about 56° C.; cooling the mixture to room temperature; maintaining the mixture at a temperature of about 4° C. for about 15 hours to obtain anhydrous aripiprazole Form II; providing a slurry of starting aripiprazole in acetone; seeding the slurry with the anhydrous aripiprazole Form II obtained from the mixture; heating the slurry at a temperature of about 25° C. to about 50° C.; and isolating aripiprazole Form II.

Another embodiment of the invention encompasses a method of preparing anhydrous aripiprazole Form II comprising: providing a mixture of aripiprazole in a solvent selected from the group consisting of: $C_3$-$C_8$ ketones, THF, acetonitrile, butyl-acetate, dimethyl formamide (DMF), a mixture of tetrahydrofuran (THF) and IPA, water, diethyl ether (DEE) and acetone; heating the mixture at a temperature of about 45° C. to about the reflux temperature; cooling the mixture to a temperature of about 10° C. to about −20° C.; maintaining the mixture for about 15 minutes to about 60 hours to obtain anhydrous aripiprazole Form II; isolating the anhydrous aripiprazole Form II; providing a slurry of aripiprazole in a solvent selected from the group consisting of: $C_3$-$C_8$ ketones, THF, acetonitrile, butyl-acetate, dimethyl formamide (DMF), a mixture of tetrahydrofuran (THF) and IPA, water, diethyl ether (DEE) and; seeding the slurry with the anhydrous aripiprazole Form II obtained from the mixture; heating the slurry at a temperature of about 25° C. to about 50° C.; and isolating aripiprazole Form II.

Another embodiment of the invention encompasses a method of preparing aripiprazole Form II comprising: combining aripiprazole and acetone to obtain a slurry; and seeding the slurry with aripiprazole Form II.

DETAILED DESCRIPTION OF THE INVENTION

Figure 1:
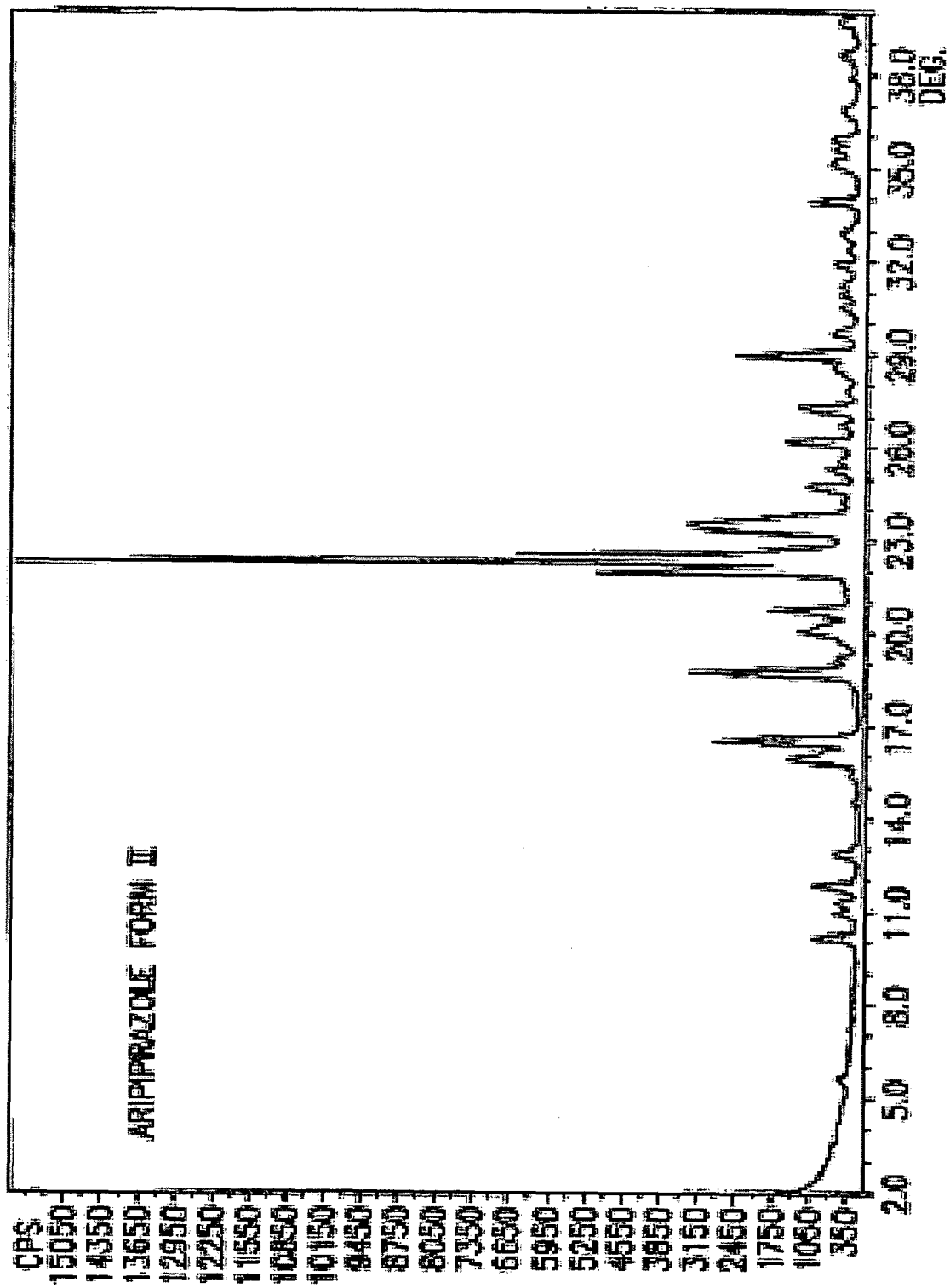
FIG. 1 illustrates the powder X-ray diffraction pattern for Form II.

The process of the invention describes slurrying aripiprazole from a low boiling solvent such as acetone. The process is reproducible and consistent such that it can be applied in the large scale manufacture of crystalline aripiprazole. During the process the slurry in acetone reduces the amounts of solvent used during crystallization, thus yielding a significant economical and ecological advantage.

Aripiprazole Form II, prepared by the method of the invention, is disclosed in WO 05/058835, hereby incorporated by reference. As disclosed therein, aripiprazole Form II is characterized by X-ray powder diffraction peaks at 16.5, 18.7, 21.9, 22.4 and 23.5 degrees two-theta±0.2 degrees two-theta. The aripiprazole crystalline Form II used for seeding can be made in situ or obtained as described in the PCT publication WO 05/058835. Aripiprazole Form XII and Compound 2 are also disclosed in WO 05/058835. As disclosed therein, aripiprazole Form XII is characterized by X-ray powder diffraction peaks at 17.4, 18.2, 19.7 and 24.5 degrees two-theta±0.2 degrees two-theta; and aripiprazole compound 2 is characterized by X-ray powder diffraction peaks at 8.8, 14.5, 17.8, 20.5 and 22.2 degrees two-theta±0.2 degrees two-theta.

The invention encompasses a method of preparing anhydrous aripiprazole Form II comprising slurrying a starting aripiprazole in a solvent selected from the group consisting of: $C_3$-$C_8$ ketones, THF, acetonitrile, butyl-acetate, dimethyl formamide (DMF), a mixture of tetrahydrofuran (THF) and IPA, water, diethyl ether (DEE) and acetone; heating the slurry; and isolating anhydrous aripiprazole Form II from the slurry. Optionally, the method can further comprise seeding the slurry with aripiprazole Form II prior to the heating step. Typically, the amount of aripiprazole Form II used for seeding is about 0.05% to 5% by weight of the aripiprazole.

Preferably, the starting aripiprazole is selected from the group consisting of: crystalline aripiprazole Form XII, Compound 2, Form C, anhydrate, hydrate, solvate and mixtures thereof.

Preferably, the solvent is acetone.

The amount of the solvent should be sufficient to form a slurry with the aripiprazole. Preferably, the ratio of starting aripiprazole to acetone is about 3:1 to about 20:1 ml of acetone per gram of aripiprazole. More preferably, the ratio of starting aripiprazole to acetone is about 3:1 to about 6:1 ml of acetone to gram of aripiprazole. Thus for example, when 30 g of aripiprazole is used 90 to 180 mL of acetone can be used.

Preferably, the slurry is heated to a temperature of about 25° C. to about 50° C. More preferably, the slurry is heated to a temperature of about 30° C. to about 50° C. Preferably, prior to the isolation step the slurry is maintained at the temperature for at least 1 hour, preferably from about 2 hours to about 22 hours.

The anhydrous aripiprazole Form II can be isolated by any method known in the art. For example, the anhydrous aripiprazole Form II can be separated by filtering the slurry or decanting the solvent from the slurry. The isolating method can further comprise washing and drying the anhydrous aripiprazole Form II. Preferably, the anhydrous aripiprazole Form II is dried at a temperature of about 30° C. to about 60° C., more preferably, at a temperature of about 40° C. to about 53° C. under reduced pressure.

Another embodiment of the invention encompasses a method of preparing anhydrous aripiprazole Form II comprising: providing a mixture of aripiprazole in a solvent selected from the group consisting of: $C_3$-$C_8$ ketones, THF, acetonitrile, butyl-acetate, dimethyl formamide (DMF), a mixture of tetrahydrofuran (THF) and IPA, water, diethyl ether (DEE) and acetone; heating the mixture at a temperature of about 45° C. to about the reflux temperature; cooling the mixture to a temperature of about 10° C. to about −20° C.; maintaining the mixture for about 15 minutes to about 60 hours to obtain anhydrous aripiprazole Form II; isolating the anhydrous aripiprazole Form II; providing a slurry of aripiprazole in a solvent selected from the group consisting of: $C_3$-$C_8$ ketones, THF, acetonitrile, butyl-acetate, dimethyl formamide (DMF), a mixture of tetrahydrofuran (THF) and IPA, water, diethyl ether (DEE) and; seeding the slurry with the anhydrous aripiprazole Form II obtained from the mixture; heating the slurry at a temperature of about 25° C. to about 50° C.; and isolating aripiprazole Form II.

Preferably, the aripiprazole used in the process is selected from the group consisting of: crystalline aripiprazole Form XII, Compound 2, Form C, anhydrate, hydrate, solvate and mixtures thereof.

Preferably, the solvent is acetone.

Preferably, the mixture is heated to a temperature of about 56° C.

Preferably, the cooling is to a temperature of about 4° C.

Preferably, the cooled mixture is maintained for about 15 hours.

Preferably, the amount of aripiprazole Form II used for seeding is about 0.05% to 5% by weight of the starting aripiprazole.

Preferably, the ratio of acetone to aripiprazole in the slurry is about 3:1 to about 20:1 ml of acetone per gram of aripiprazole. More preferably, the ratio of acetone to aripiprazole in the slurry is about 3:1 to about 6:1 ml of acetone per gram of aripiprazole.

The slurry can be prepared using the conditions and reagents described above.

Aripiprazole Form II can be isolated using the methods described above.

Another embodiment of the invention encompasses a method of preparing aripiprazole Form II comprising: combining aripiprazole and acetone to obtain a slurry; and seeding the slurry with aripiprazole Form II.

Having described the invention with reference to certain preferred embodiments, other embodiments will become apparent to one skilled in the art from consideration of the specification. The invention is further defined by reference to the following examples describing in detail the analysis of the aripiprazole crystalline forms and methods for preparing the crystalline forms of the invention. It will be apparent to those skilled in the art that many modifications, both to materials and methods, may be practiced without departing from the scope of the invention.

EXAMPLES

Examples 1-13

Preparation of Aripiprazole Form II by Slurry in Acetone Including Seeding of Aripiprazole Form II The starting aripiprazole in crystalline form (30 g), acetone (90-180 ml) and aripiprazole Form II (0.015 to 1.5 g) were introduced into a 250 ml reactor. The mixture was heated at 25° C. to 50° C. and stirred for at least 1 hr. Then, the mixture was cooled to room temperature and stirred for at least 10 min. The precipitate, wet aripiprazole Form II, was collected by filtration and washed with 30 ml of acetone. The wet aripiprazole Form II was dried under vacuum at 40° C. to 53° C. overnight. Dry aripiprazole Form II was obtained. The results are summarized in Table 1.

| Exp No. | Polymorph before slurry | V | Description Temp | hr | seeding | Polymorph after slurry (wet) | Polymorph after slurry (Dry) |
|---|---|---|---|---|---|---|---|
| 1 | (wet) XII | 3 | 25° C. | 4 | 5% | Form II | |
| 2 | | | | 8 | | Form II | Form II |
| 3 | | | | 22 | | Form II | Form II |
| 4 | (wet) XII | 3 | 50° C. | 4 | 5% | Form II | |
| 5 | | | 25° C. | 8 | | Form II | Form II |
| 6 | | | | 22 | | Form II | |
| 7 | (wet) XII | 3 | 40° C. | 2 | 1% | Form II | Form II |
| 8 | (wet) XII | 3 | 50° C. | 2 | 1% | Form II | Form II |
| 9 | Hydrate + XII | 3 | 50° C. | 4 | 1% | Form II | Form II |
| 10 | Hydrate + XII | 3 | 50° C. | 4 | 5% | Form II | Form II |
| 11 | Compound 2 | 3 | 25° C. | 6 | 0.5% | | Form II |
| 12 | Compound 2 + C (20%) (dry) | 3 | 25° C. | 2.5 | 0.5% | | Form II |
| 13 | Compound 2 >>>C (dry) | 3 | 25° C. | 3 | 5% | Form II | Form II |

Example 14

Preparation of Aripiprazole Form II by Slurry in Acetone Including Seeding of Aripiprazole Form II Aripiprazole Form XII (10.8 Kg wet or 10 Kg dry), acetone (40 L) and aripiprazole Form II (200 g) were introduced into 100 L reactor. The mixture was heated to 48° C. and stirred for 2 hr. Then, the mixture was cooled to room temperature and stirred for 1 hour. Aripiprazole Form II was collected by filtration and washed with 10 L of acetone. The wet aripiprazole Form II was dried under vacuum at 49° C. for 4 hours. 9.5 Kg of dry aripiprazole Form II was obtained.

What is claimed is:

1. A method of preparing anhydrous aripiprazole Form II comprising: slurrying a starting aripiprazole in acetone; heating the slurry; and isolating anhydrous aripiprazole Form II from the slurry.

2. The method according to claim 1 further comprising seeding the slurry with aripiprazole Form II prior to heating.

3. The method according to claim 2, wherein the amount of aripiprazole Form II used for seeding is about 0.05% to 5% by weight of the starting aripiprazole.

4. The method according to claim 1, wherein the starting aripiprazole is selected from the group consisting of: crystalline aripiprazole Form XII, Compound 2, Form C, anhydrate, hydrate, solvate and mixtures thereof.

5. The method according to claim 1, wherein the ratio of acetone to aripiprazole is 3:1 to about 20:1 ml of acetone to gram of starting aripiprazole.

6. The method according to claim 5, wherein the ratio of acetone to aripiprazole is about 3:1 to about 6:1 ml of acetone to gram of starting aripiprazole.

7. The method according to claim 1, wherein the heating to a temperature of about 25° C. to about 50° C.

8. The method according to claim 7, wherein the heating is carried out at a temperature of about 30° C. to about 50° C.

9. The method according to claim 1, further comprising maintaining the slurry prior to the isolation step.

10. The method according to claim 9, wherein the slurry is maintained for at least 1 hour.

11. The method according to claim 10, wherein the slurry is maintained for about 2 hours to about 22 hours.

12. The method according to claim 1, wherein the isolation is by filtering the slurry.

13. The method according to claim 1, wherein the isolation is by decanting the solvent from the slurry.

14. The method according to any of claims 12 and 13, further comprising washing and drying the anhydrous aripiprazole Form II.

15. The method according to claim 14, wherein the anhydrous aripiprazole Form II is dried at a temperature of about 30° C. to about 60° C. under reduced pressure.

16. The method according to claim 15, wherein the anhydrous aripiprazole Form II is dried at a temperature of about 40° C. to about 53° C. under reduced pressure.

* * * * *